United States Patent [19]

Yokoyama et al.

[11] Patent Number: 4,797,153

[45] Date of Patent: Jan. 10, 1989

[54] METHOD OF INCREASING BIOMASS IN PLANTS

[75] Inventors: Henry Yokoyama, Pasadena; Wan-Jean Hsu, San Marino; Stephen M. Poling, Arleta; Ernest P. Hayman, Pasadena, all of Calif.

[73] Assignee: The United States of America as represented by the Secretary of Agriculture, Washington, D.C.

[21] Appl. No.: 701,660

[22] Filed: Feb. 15, 1985

Related U.S. Application Data

[63] Continuation-in-part of Ser. No. 435,597, Oct. 21, 1982, abandoned.

[51] Int. Cl.$^4$ ............................................. A71N 33/04
[52] U.S. Cl. ............................................. 71/121; 71/88
[58] Field of Search ......................................... 71/121

[56] References Cited

U.S. PATENT DOCUMENTS

| | | | |
|---|---|---|---|
| 3,078,152 | 2/1963 | Weiss et al. | 71/121 |
| 3,833,350 | 7/1974 | Cooke et al. | 71/98 |
| 3,864,501 | 2/1975 | Yokoyama et al. | 428/268 |
| 3,911,148 | 10/1975 | Yokoyama et al. | 426/268 |
| 3,911,152 | 10/1975 | Yokoyama et al. | 426/268 |
| 4,159,903 | 7/1979 | Bauman | 71/98 |
| 4,204,859 | 5/1980 | Yokoyama et al. | 71/121 |
| 4,363,188 | 12/1982 | Lovelace et al. | 47/58 |

OTHER PUBLICATIONS

Gonzalez et al., Chem. Abst. vol. 92, (1980), 70925d.
Choudbri et al., Chem. Abst., vol. 78, (1973), 12631e.
Apelbaum et al., Chem. Abst. vol. 77, (1972) 110500k.
Dasroor et al., Chem. Abstr., vol. 95, (1981), 1739w.
S.-L. Lee et al., "Effects of Bioregulators on Indole Alkaloid Biosynthesis in *Catharanthus Roseus* Cell Culture," *Phytochemistry*, vol. 20, pp. 1841-1843 (1981).
Schuetz and Baldwin, "The Synthesis and Properties of Some Substituted Phenyl w-(N,N-Dialkylamino)-alkyl Sulfides," *Journal of the American Chemical Society*, vol. 80, pp. 162-164 (1958).
*Official Methods of the Association of Official Analytical Chemists*, 13th Edition, Ed. by W. Horowitz, AOAC, Washington, D.C. (1980), pp. 931-937.
E. Layne, "Spectrophotometric and Turbidimetric Methods for Measuring Proteins," *Methods in Enzymology*, vol. 3, pp. 447-454, Academic Press, Inc., (1957) New York.
Torton and Whitaker, "Evaluation of the Biuret and Dye-Binding Methods for Protein Determination in Meats," *Journal of Food Science*, vol. 29, p. 168 (1964).
*The Essential Oils*, by E. Guenther, vol. 1, pp. 285-291, D. Van Nostrand Company, Inc., New York (1948).

*Primary Examiner*—Catherine L. Mills
*Attorney, Agent, or Firm*—M. Howard Silverstein; John D. Fado; Margaret A. Connor

[57] ABSTRACT

A method of increasing plant biomass, individual plant constituents, and in most cases, increasing rate of plant growth, by the application of certain substituted phenoxytrialkylamines, substituted phenylthiotrialkyamines or dialkylmorpholium halides to plants at very early stages of development and in very low amounts.

15 Claims, No Drawings

METHOD OF INCREASING BIOMASS IN PLANTS

This is a continuation-in-part of application Ser. No. 435,597, filed Oct. 21, 1982, now abandoned.

BACKGROUND OF THE INVENTION

The present invention relates to and has among its objects the provision of novel processes for increasing growth rate, total biomass and amount of individual constituents in plants. Further objects of the invention will be evident from the following description wherein parts and percentages are by weight unless otherwise specified.

Increase in world population has greatly increased the demand for food, fiber and renewable energy sources, while at the same time limiting the amount of acreage available for crop production. It is increasingly becoming of concern whether agricultural crop productivity can keep pace with increasing population and at the same time provide renewable energy resources. Approaches for increasing food production and crop yield include breeding and selecting more productive plant varieties, improvement of farm management, and use of fertilizers, herbicides and pesticides. These methods have been useful in increasing production in technologically advanced countries but have had limited impact on developing nations where cultural practices and farm management are not advanced and where the cost of fertilizer prohibits the use. Additionally, even with these methods, productivity of the major agricultural crops within the United States has somewhat leveled off in the past decade.

Past agricultural research has given little attention to the control of the biological processes that limit crop productivity and quality, thus much of the biological potential of plants has gone untapped. Although certain bioregulatory compounds and use thereof have been reported which increase particular plant constituents such as polyisoprene in guayule or Hevea rubber plants or carotenoid pigment in citrus, tomatoes and the like (U.S. Pat. Nos. 3,833,350; 4,159,903; 4,204,859; 3,864,501; 3,911,148 and 3,911,152), such increases are primarily at the expense of other plant constitutents and little or no increase in total plant biomass has resulted from these inventions.

SUMMARY OF THE INVENTION

We have found that application of particular compounds to plants at very early stages of development and at very low levels increases plant biomass, causes enhancement of plant constituents and in most cases increases rate of plant growth. In the method of the invention, the compounds of the invention are applied in bioregulatory amounts to plant seeds, seedlings or plant buds at an early stage of development in an amount sufficient to increase biomass but insufficient to cause harm to the plant. Compounds used in our method are selected from groups having the structure

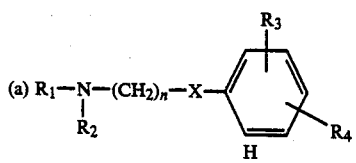

wherein:
X is either oxygen or sulfur,
$R_1$ and $R_2$ are lower alkyl containing 1 to 3 carbon atoms,
n is an integer from 1 to 3, and
$R_3$ and $R_4$ are independently hydrogen, chlorine, bromine, iodine, lower alkyl containing 1 to 6 carbon atoms, lower alkoxy containing 1 to 6 carbon atoms, or condensed mono- and polycyclic aromatic ring systems, and wherein:
if $R_3$ and $R_4$ are 3,5,-substitutents, then the lower alkyl or alkoxy group must contain 3 to 6 carbon atoms; and wherein:
if $R_3$ is hydrogen, then $R_4$ must be a 4-substituent, with the proviso that $R_4$ is other than hydrogen;
(b) an acid addition salt of the compounds defined above; and (c) 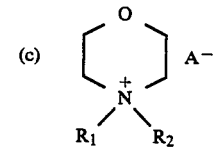

wherein:
A is the anion derived from an acid added to the amine to form a salt and $R_1$ and $R_2$ are as defined above.

Application of the compounds of the invention causes treated plants to have increased capacity to form and store valuable plant constituents over untreated plants. Thus plants which develop under the influence of the bioregulatory compounds of the invention have greater biomass than untreated plants resulting in increased agricultural crop production per unit area.

Additionally, other plant constituents important for food, fiber and renewable energy sources such as protein, lipid, sugar, essential oils, plant fibers and the like are increased using the method of the invention. Since total biomass is increased, the increase of these individual constituents is not at the expense of other valuable constituents as occurs in the prior art methods.

Another advantage of the invention is that in most cases growth rate of the treated plant is increased over untreated plants resulting in accelerated maturation. This is advantageous because shorter growing periods decrease the labor and cost of production, decrease the use of energy such as fossil fuel sources used for fertilizers and in some cases make it possible to plant additional crops in a crop year.

DESCRIPTION OF THE PREFERRED EMBODIMENTS

As mentioned above, the benefits of the invention are obtained by applying any of the aforementioned compounds to plant seeds, seedlings or buds. Examples, by way of illustration and not limitation, of compounds that can be used in the process of the invention are:

A. (2,4-Substituted phenoxy)alkyldialkylamines wherein the 2,4-substituents are independently chloro, bromo, iodo, methyl, ethyl, propyl, butyl, pentyl, hexyl, methoxy, ethoxy, propoxy, butoxy, pentoxy or hexoxy, and wherein the alkyl and dialkyl groups are independently either, methyl, ethyl or propyl.

B. (3,5,-Substituted phenoxy)alkyldiakylamines wherein the 3,5-substituents are independently chloro, bromo, iodo, propyl, butyl, pentyl, hexyl, propoxy, butoxy, pentoxy or hexoxy, and wherein the alkyl and dialykl groups are the same as those in A.

C. (3,4-Substituted phenoxy)alkyldialkylamines wherein the 3,4-substituents are independently chloro, bromo, iodo, methyl, ethyl, propyl, butyl, pentyl, hexyl, methoxy, ethoxy, propoxy, butoxy, pentoxy or hexoxy, and wherein the alkyl and dialkyl groups are the same as those in A.

D. (4-Substituted phenoxy)alkyldialkylamines wherein the 4-substituent is either methyl, ethyl, propyl, butyl, pentyl, hexyl, methoxy, ethoxy, propoxy, butoxy, pentoxy or hexoxy, and wherein the alkyl and dialkyl groups are the same as those in A.

E. (Naphthoxy)alkyldialkylamines wherein the alkyl and dialkyl groups are the same as those in A.

F. Dialkylmorpholium halides wherein the anion is chloride, bromide or iodide and the dialkyl groups are the same as those in A.

For the method disclosed in the invention, the preferred compounds in groups A through E are those wherein n is 2, X is oxygen, the dialkyl groups are diethyl and the phenoxy substituents are 2,4-dichloro; 3,4-dichloro; 3-5-diisopropyl; 3,5,-ditertiary butyl; 3,4-dimethyl; 3,4-dimethoxy; 3-methyl, 4-chloro; or 3,4-naphthoxy. For compounds in group F, the preferred dialkyl groups are methyl and the preferred halide is iodide.

Various acid addition salts of the above compounds are readily produced. For example, by adding acid to the compounds of the invention, the following acid addition salts are formed:

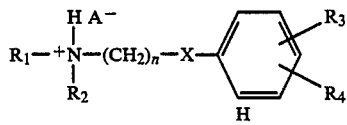

wherein:
X is either oxygen or sulfur,
$R_1$ and $R_2$ are lower alkyl containing from 1 to 3 carbon atoms,
n is an integer from 1 to 3,
$R_3$ and $R_4$, are independently hydrogen, chlorine, bromine, iodine, lower alkyl containing from 1 to 6 carbon atoms, lower alkoxy containing from 1 to 6 carbon atoms, or condensed mono- and polycyclic aromatic ring systems; and wherein:
if $R_3$ and $R_4$ are 3,5-substituents, then the lower alkyl or alkoxy group must contain 3 to 6 carbon atoms; and wherein:
if $R_3$ is hydrogen, then $R_4$ must be a 4-substituent, with the provisio that $R_4$ is other than hydrogen; and wherein:
A is the anion derived from the acid added to the amine to form a salt.

In order to achieve increase in total biomass yield, enhancement of individual plant constituents or increase in rate of plant growth, the compounds of the invention must be first applied to the plant at an early stage of development, that is, immediately prior to, or at the time when cell differentiation and plant growth are great. If application is made at a late stage of development some increase in yield or plant constituents may occur but not the significant increase which occurs where treatment is earlier. As a practical matter, treatment is made to the seed; to the post-emergent seedling plant, that is, to the plant at or prior to the full expansion of the fourth set of primary leaves, such as at the cotyledon, true leaf, two-leaf or four-leaf stage; or to trees during flower bud swell or a week before or after. For plants which are not grown from seed or do not produce flower buds such as vegetatively propagated plants like sugarcane, application should be at the developmental growth stages equivalent to the ones aforementioned. Since growth of the plant or tree dilutes the concentration of the bioregulatory compound due to increase in plant biomass (biomass dilution effect), it may be desirable to apply more than one application subsequent to the initial one. Subsequent applications should be made before completion of cell differentiation of the growing plant or when applied to a growing tree before the completion of cell differentiation of the growing fruit.

The effective amount of the compound to be applied so as to achieve the increase in biomass contemplated by the invention varies depending upon the stage of the plant's development when application is made, on whether the plant is grown in the field or greenhouse, the degree of penetration of the plant by the bioregulator, and whether or not a penetrating agent is used.

Generally, where the compounds are applied to the seeds, the concentration is about 0.005 to 0.3 mg of active ingredient per seed. Application is conveniently made by dissolving the compound to be used in water at a concentration of 5 to 50 parts per million (ppm) in the diluent and soaking the seeds for about 2 to 6 hours. Other means of treatment of seeds such as encapsulation of the seeds with the compounds by conventional methods are encompassed by the invention.

When application is made to the seedling, that at the cotelydon, true leaf, two-leaf or four-leaf stages and the like the treatment is about 0.005 mg to 0.3 mg active ingredient per plant. This can be accomplished by using a treatment rate of about 5 to 200 ppm and preferably 5 to 120 ppm. Treatment rates are critical. Use of treatment rates of 300 ppm or greater on young seedlings or young plants, that is, prior to the full expansion of the fourth set of primary leaves, will either not cause increases in biomass contemplated by the invention or in many cases, may have a phytotoxic effect on the plant causing it to have stunted growth.

Treatment of perennial trees requires a greater amount of the bioregulator compound due to the greater mass of the tree. Generally, about one to four grams active ingredient per tree is applied using a treatment rate of 50 to 500 ppm of bioregulatory compound.

The compounds of the invention may be applied to the plant in any convenient manner suggested to those skilled in the art. For example, the compound after being dissolved in water, can be sprayed onto the branches and leaves of the plant. Other application techniques known to the skilled artisan may be employed.

Appropriate wetting agents such as Triton X-100 (polyethylene glycol p-isooctylphenylether made by J. T. Baker), ORTHO X-77 (a mixture of fatty acids, fatty alcohols and isopropanol made by Chevron Chemical Company), Sweep 4F (chlorothalonil from Diamond Shamrock Company) and the like may be added to the aqueous solution to aid in plant treatment. Appropriate penetrating agents such as B-cyclodextrin (B-(heptamer)-cyclodextrin made by Takeda Chemical Industries, Ltd.) may be added to the aqueous solution to increase penetration of the bioregulatory compound.

Without any intention of limiting the scope of the invention, it is theorized that the compounds used in the method of the invention play a role in the photosynthetic pathway in green plants. It is theorized that application of the compounds to the developing green plant causes increased assimilation of carbon dioxide in the photosynthetic pathway thereby increasing the carbon atoms available for synthesis of total biomass and individual plant constituents. It is further theorized that use of the compounds at an early stage of plant or fruit development and before completion of cell differentiation manipulates the genetic expression of the plant so as to tap unused biological potential. Thus as new cells develop under the influence of the bioregulatory compounds, they possess increased capacity to form and store valuable materials and to form increased amount of plant tissues.

As noted above, some compounds of the same or similar chemical structure have been used to enhance polyisoprene production in rubber plants and/or to induce accumulation of carotenoids in citrus. When used according to methods which cause enhancement of isoprene or carotenoid induction, little or no increase in biomass occurs and increase in rubber or color compounds are at the expense of other plant constituents such as starch or lipid, that is, there is a negative correlation between rubber or carotenoid increase and content of other constituents. In the method of increasing carotenoids in fruits and vegetables which contain carotenogenic tissue, application of the bioregulator is either post harvest or about ten days prior to harvest. Such a method of application will not achieve the biomass increases of the present invention. Furthermore certain compounds which act to increase carotenoids in citrus such as 2-diethylaminoethyl-4-methylphenylether, 2-diethylaminoethyl-4-chlorophenylether and 2-diethylaminoethylhexanoate will not increase total biomass when used according to the present invention.

To increase rubber content in guayule, compounds are applied at a rate of 300 to 10,000 ppm to 4-month or 8-month old plants. Application of these amounts to seeds or seedlings according to the present invention results either in no effect or in phytotoxic effects to the seedlings. Additionally, certain compounds such as N,N-dimethylmorpholium iodide increase biomass in the instant invention but do not increase the rubber content of guayule. Other compounds such as 2-(2,4-dichlorophenoxy)triethylamine do not increase guayule rubber production when applied at the preferred treatment rates for young plants, ie below 300 ppm. Conversely, certain compounds, such as $(CH_3CH_2)_2N(CH_2)_q$ phenyl where $q=1$ to $5$ do not increase biomass in the method of the instant invention but enhance the polyisoprene content of guayule.

As stated above, the compounds of the invention when applied in accordance with the method of the invention, substantially increase total biomass, enhance the amount of some or all plant constituents and in many cases increase the rate of growth in green plants over untreated plants as long as constituents such as water and light which are necessary for plant growth are present in the required amount.

For example, in sugar beets, the rate of growth, total biomass, and yield of sugar per acre are increased using the method of the invention. Cereal grains such as corn, rye, wheat, rice, barley, crops such as cuphea, cotton and the like and legumes such soybeans and cowpeas and the like show increases in growth rate, total biomass and protein and lipid content. Calotropis shows increase in biomass and latex content. Treatment of citrus trees causes the fruit to mature faster and have increased biomass and content of essential oils. A few examples of other plants which exhibit increased growth rate, biomass and amount of constituents includes vegetables such as tomatoes, lettuce, spinach and the like; seed plants such as sunflower and plants such as crambe. Thus, the method of invention finds use on any green plant where increased rate of growth, biomass or the like is desired. The method is particularly valuable for use on plants which produce food, fiber, or energy; or plants, such as crambe, where commercial production is limited due to low plant yield when grown without bioregulators.

The compounds of the invention may be prepared according to known procedures as outlined by Schuetz and Baldwin in the *Journal of the American Chemical Society*, Volume 80. p. 162 (1958). The general reaction scheme may be outlined as follows:

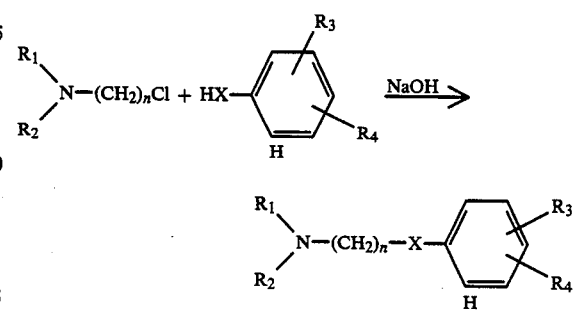

Dimethylmorpholium halide is synthesized by treating methylmorpholine with methyl halide.

EXAMPLES

The invention is further demonstrated by the following illustrative examples.

EXAMPLES I

The hydrochloric acid salts of the compounds 2-(2,4-dichlorophenoxy)triethylamine (2,4-DCTA), 2-(3,4-dichlorophenoxy)triethylamine (3,4-DCTA), 2-(3,4-diisopropylphenoxy)triethylamine (DITA), and 2-(2-napthoxy)triethylamine (NTA) were synthesized from 2-diethylaminoethyl chloride and 2,4-dichlorophenol, 3,4-dichlorophenol, 3,4-diisopropylphenol and naphthol, respectively, according to the procedure of Schuetz and Baldwin as outlined above.

Sugar beets (var. SS-X811E) were direct seeded in a field consisting of 8 by 200 feet rows. Eight by 7-foot plots were treated and the plots were randomized. The plots were thinned to about 8 to 10 inches when the sugar beet leaves reached approximately 6 inches in height (about 6 weeks after planting).

An aqueous dispersion containing 80 or 100 ppm of the bioregulator and 10 ppm of Triton X100 in water was prepared. The sugar beets were initially sprayed with the above solution at the cotyledon stage (seven days after planting) and two additional times three and six weeks after the initial application. Control plants were grown which were sprayed only with 10 ppm of Triton X100 in water at the same intervals as the treated plants. The inside six rows of the treated and control plants were harvested twice, at five and six months after planting. Each harvest was analyzed for net weights of total plant and sugar beet root and percent sugar (as sucrose content). Sugar content was determined using the refractive index method according to the *Official Methods of the Association to Official Analytical Chemists*, 13th Edition, Ed. by W. Horwitz, AOAC, Washington, D.C. (1980), pp. 931–937.

The yield of sugar on a ton per acre was determined. Samples A and B each represent the average of four replicate treatment plots.

Increases in sugar yield over the controls ranged from 33 to 83 percent ton per acre. Results are tabulated in Table IA (first harvest) and Table IB (second harvest).

and 100 ppm of bioregulatory compound in water containing 10 ppm Triton X-100 were sprayed on the soybean plants at the cotyledon stage (ten days after planting) at a rate of about 0.2 to 0.3 mg active ingredient per plant. Two subsequent application at these levels were made at three and six weeks after the initial treatment. The beans were harvested at maturity.

Protein content was determined on a 2.0 g defatted plant sample according to the method described by E. Layne, *Methods in Enzymology*, Volume 3, pp 447–454, Ed. S. P. Colowick and N. O. Kaplan, Academic Press, New York (1957) and Torton and Whitaker, *Journal of Food Science*, Volume 29, p 168 (1964).

Lipid content was determined as follows: dehulled soybeans, dried at 60° C. in a vacuum oven, were

TABLE IA

| Sample No. | Treatment ppm | Sugar (%) A | B | Ave | Net Weight ton/acre A | B | Ave | Root Weight A | A | Ave. | Sugar Yield sugar × root weight (ton/acre) | Increase Over Control (%) |
|---|---|---|---|---|---|---|---|---|---|---|---|---|
| 1 | Control | 11.2 | 11.5 | 11.35 | 15.8 | 18.9 | 17.4 | 13.8 | 16.5 | 15.2 | 1.725 | |
| 2 | 2,4-DCTA 100 ppm | 11.0 | 11.3 | 11.15 | 28.8 | 30.2 | 29.5 | 20.9 | 26.4 | 23.6 | 2.643 | 53.3 |
| 3 | 2,4-DCTA 80 ppm | 10.9 | 11.5 | 11.2 | 34.7 | 24.6 | 29.6 | 30.3 | 21.5 | 25.9 | 2.901 | 68.2 |
| 4 | 3,4-DCTA 100 ppm | 11.5 | 11.1 | 11.3 | 35.7 | 28.3 | 30.2 | 31.2 | 24.8 | 28.0 | 3.164 | 83.4 |
| 5 | 3,4-DCTA 80 ppm | 10.9 | 10.2 | 10.5 | 28.1 | 20.4 | 24.2 | 24.6 | 17.8 | 21.2 | 2.226 | 29.0 |
| 6 | DITA 100 ppm | 11.4 | 11.2 | 11.3 | 28.5 | 31.7 | 30.1 | 24.9 | 27.7 | 26.3 | 2.972 | 72.3 |
| 7 | DITA 80 ppm | 11.7 | 10.3 | 11.0 | 27.3 | 27.9 | 27.6 | 23.9 | 24.4 | 24.2 | 2.662 | 54.3 |
| 8 | NTA 100 ppm | 10.8 | 10.3 | 10.55 | 28.0 | 33.4 | 30.7 | 22.8 | 29.2 | 26.0 | 2.743 | 59.0 |
| 9 | NTA 80 ppm | 11.3 | 11.5 | 11.4 | 27.7 | 22.9 | 25.3 | 24.2 | 20.0 | 22.1 | 2.519 | 46.0 |

TABLE IB

| Sample | Treatment ppm | Sugar (%) A | B | Ave | Net Weight ton/acre A | B | Ave | Root Weight ton/acre A | B | Ave | Sugar Yield Sugar × root weight (ton/acre) | Increase Over Control (%) |
|---|---|---|---|---|---|---|---|---|---|---|---|---|
| 1 | Control | 13.2 | 13.4 | 13.3 | 20.7 | 20.9 | 20.8 | 22.5 | 22.7 | 22.6 | 3.005 | |
| 2 | 2,4-DCTA 100 ppm | 13.1 | 13.1 | 13.1 | 21.7 | 23.4 | 22.6 | 23.6 | 25.4 | 24.5 | 3.210 | 6.8 |
| 3 | 2,4-DCTA 80 ppm | 14.5 | 14.0 | 14.2 | 19.3 | 21.4 | 20.4 | 21.0 | 23.3 | 22.2 | 3.152 | 4.9 |
| 4 | 3,4-DCTA 100 ppm | 12.9 | 14.3 | 13.6 | 25.9 | 23.7 | 24.8 | 28.2 | 25.8 | 27.0 | 3.672 | 22.2 |
| 5 | 3,4-DCTA 80 ppm | 13.6 | 14.0 | 13.8 | 27.7 | 25.5 | 26.6 | 30.1 | 27.7 | 28.9 | 3.988 | 32.7 |
| 6 | DITA 100 ppm | 13.5 | 13.5 | 13.5 | 26.5 | 21.6 | 24.0 | 28.8 | 23.5 | 26.2 | 3.537 | 17.7 |
| 7 | DITA 80 ppm | 13.1 | 12.7 | 12.9 | 28.2 | 25.5 | 26.8 | 30.6 | 27.2 | 29.2 | 3.767 | 25.4 |
| 8 | NTA 100 ppm | 13.0 | 12.8 | 12.9 | 36.8 | 30.3 | 33.6 | 40.0 | 32.9 | 36.4 | 4.696 | 56.3 |
| 9 | NTA 80 ppm | 13.3 | 12.0 | 12.6 | 25.5 | 24.4 | 25.0 | 27.7 | 26.5 | 27.1 | 3.415 | 13.6 |

EXAMPLE 2

The hydrochloric acid salts of 2,4-DCTA, 3,4-DCTA, and DITA, and N,N-dimethylmorpholium iodide (DMI) were prepared as described above.

Soybeans (var. Centennial) were direct seeded in plots as described in Example 1. Concentrations of 80 and 100 ppm of bioregulatory compound in water containing 10 ppm Triton X-100 were sprayed on the soybean plants at the cotyledon stage (ten days after planting) at a rate of about 0.2 to 0.3 mg active ingredient per plant. Two subsequent application at these levels were made at three and six weeks after the initial treatment. The beans were harvested at maturity.

ground to pass a 40-mesh screen and extracted 8 hours in petroleum ether in a soxhlet apparatus. The weight of oil extracted was measured.

Increase in protein content ranged from 17.5 to 67.5 percent. Lipid increased 2.5 to 29 percent. Total yield on a grams per plot basis increased 4 to 35 percent. The results are tabulated in Table II.

TABLE II

| Sample | Treatment ppm | Lipid % A | B | Ave | % Increase Over Control | Protein (%) A | B | Ave | % Increase Over Control | Yield (gm/plot) A | B | Ave | % Increase Over Control |
|---|---|---|---|---|---|---|---|---|---|---|---|---|---|
| 1 | Control | 13.42 | 14.12 | 13.77 | | 22.57 | 20.89 | 21.73 | | 2977.3 | 3285.4 | 3131.4 | |
| 2 | 2,4-DCTA | 16.82 | 16.28 | 16.55 | 20.2 | 36.27 | 36.84 | 36.55 | 67.5 | 4081.2 | 4384.7 | 4233.0 | 35.2 |

TABLE II-continued

| Sample | Treatment ppm | Lipid % A | B | Ave | % Increase Over Control | Protein (%) A | B | Ave | % Increase Over Control | Yield (gm/plot) A | B | Ave | % Increase Over Control |
|---|---|---|---|---|---|---|---|---|---|---|---|---|---|
| 3 | 2,4-DCTA 100 ppm | 14.25 | 13.99 | 14.12 | 2.5 | 24.33 | 26.73 | 25.53 | 17.5 | 3117.3 | 3400.2 | 3258.8 | 4.1 |
| 4 | 3,4-DCTA 80 ppm | 14.47 | 15.02 | 15.00 | 8.9 | 35.21 | 34.89 | 35.05 | 61.3 | 3613.8 | 3721.9 | 3721.9 | 17.7 |
| 5 | 3,4-DCTA 100 ppm | 15.07 | 15.67 | 15.37 | 11.6 | 27.39 | 29.01 | 28.20 | 29.8 | 3440.2 | 3958.5 | 3699.4 | 18.1 |
| 6 | DITA 80 ppm | 17.90 | 17.57 | 17.74 | 28.8 | 25.28 | 27.00 | 26.14 | 20.3 | 3686.2 | 4170.7 | 3928.0 | 25.5 |
| 7 | DITA 100 ppm | 15.07 | 15.38 | 15.23 | 10.6 | 30.11 | 32.65 | 31.38 | 44.4 | 3785.7 | 3958.5 | 3872.1 | 23.7 |
| 8 | DMI 80 ppm | 17.82 | 18.12 | 17.82 | 29.41 | 29.79 | 31.81 | 30.80 | 41.7 | 3833.1 | 4349.0 | 4091.1 | 30.6 |
| 9 | DMI 100 ppm | 15.99 | 16.23 | 16.11 | 17.0 | 23.93 | 27.49 | 25.71 | 18.3 | 4027.1 | 4385.4 | 4206.3 | 34.3 |

EXAMPLE 3

The acid salts of 2-(3,4-dimethylphenoxy)triethylamine (DMTA), 3-4-DCTA, 2-(3-methyl, 4-chlorophenoxy)triethylamine (MCTA), and 2-(3,4-dimethoxyphenoxy)triethylamine (DMOTA) were prepared as described above.

Eight lots of lemon trees (150–200 pounds of fruit per lot) were treated with 125, 250 or 500 ppm bioregulator and 250 ppm Triton X100 in water. The initial application was at the flower bud stage, with subsequent applications at 2½ months intervals after the previous application until harvesting of the fruit 13 months later. The control was 250 ppm Triton X100 in water. Yield of lemon essential oil based on cold pressed oil and lemon oil quality based on total aldehyde content as citral was measured. Aldehyde content was determined using the hydroxylamine titration method described in *The Essential Oils*, by E. Guenther, Volume 1, pp 285–291, D. Van Nostrand Company, Inc., New York (1948). Essential oil was determined by cold pressing of the fruit peel.

Use of the method of the invention increased available oil 25 to 69 percent over the control. Total aldehyde content increased 13 to 44 percent. The results are tabulated in Table III.

TABLE III

| Lot | Treatment ppm | Available Oil lbs/ton | % Increase | Total Adehyde as Citral % | % Increase |
|---|---|---|---|---|---|
| 1 | Control | 9.26 | | 2.80 | |
| 2 | DMTA 500 ppm | 13.10 | 41.5 | 3.76 | 34.3 |
| 3 | DMTA 250 ppm | 11.70 | 26.3 | 3.56 | 27.1 |
| 4 | 3,4-DCTA 250 ppm | 15.70 | 69.5 | 4.04 | 44.3 |
| 5 | 3,4-DCTA 125 ppm | 12.60 | 36.1 | 3.58 | 27.9 |
| 6 | MCTA 500 ppm | 14.30 | 54.4 | 3.56 | 27.1 |
| 7 | MCTA 250 ppm | 12.80 | 38.2 | 3.16 | 12.9 |
| 8 | DMOTA 250 ppm | 11.6 | 25.3 | 3.62 | 29.3 |

Having thus described our invention, we claim:

1. A method for increasing total plant biomass which comprises applying to a plant immediately prior to or at a time when cell differentiation and growth of the plant or flower buds are great, that is, to the plant seed, to the plant seedling prior to the full expansion of the fourth set of primary leaves, or to trees during a week before or after flower bud swell, a bioregulatory compound in an amount sufficient to increase total biomass, i.e., in an amount sufficient to increase individual constituents of the plant but insufficient to cause harm to the plant, wherein said constituents are selected from the group consisting of protein, lipid, sugar, and essential oil, and wherein said compound is applied in an amount of about 0.005 to 0.3 mg active ingredient per plant seed or seedling or about 1 to 4 grams active ingredient per tree, said compound selected from the group having the structure

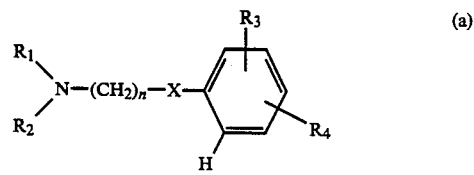

wherein:
X is either oxygen or sulfur,
$R_1$ and $R_2$ are lower alkyl containing from 1 to 3 carbon atoms,
n is an integer from 1 to 3,
$R_3$ and $R_4$ are independently hydrogen, chlorine, bromine, iodine, lower alkyl containing from 1 to 6 carbon atoms, lower alkoxy containing from 1 to 6 carbons, or condensed benzene ring, and wherein:
if $R_3$ and $R_4$ are 3,5-substituents, then the lower alkyl or alkoxy group contain 3 to 6 carbon atoms; and wherein;
if $R_3$ is hydrogen, the $R_4$ must be a 4-substituent, with the proviso that $R_4$ is other than hydrogen; and
(b) and acid addition salt thereof.

2. The method of claim 1 wherein said group of constituents consists further of fiber.

3. The method of claim 1 wherein said plant is a cereal grain.

4. The method of claim 1 wherein said plant is a legume.

5. The method of claim 1 where said plant is a citrus tree.

6. The method of claim 1 wherein said plant is a vegetable plant.

7. The method of claim 1 wherein the compound is 2(2,4-dichlorophenoxy)triethylamine or an acid salt thereof.

8. The method of claim 1 wherein the compound is 2-(3,4-dichlorophenoxy)triethylamine or an acid salt thereof.

9. The method of claim 1 wherein the compound is 2-(3,4diisopropylphenoxy)triethylamine or an acid salt thereof.

10. The method of claim 1 wherein the compound is 2-(2-napthoxy)triethylamine or an acid salt thereof.

11. The method of claim 1 wherein the compound is 2-(3,4-dimethylphenoxy)triethylamine or an acid salt thereof.

12. The method of claim 1 wherein the compound is 2-(3-methyl, 4-chlorophenoxy)triethylamine or an acid salt thereof.

13. The method of claim 1 wherein the compound is 2-(3,4-dimethoxyphenoxy)triethylamine or an acid salt thereof.

14. The method of claim 1 wherein said bioregulatory compound is applied as an aqueous dispersion.

15. The method of claim 1 wherein said bioregulatory compound is applied to the plant more than once.

* * * * *